United States Patent
Moon et al.

(10) Patent No.: US 12,207,990 B2
(45) Date of Patent: Jan. 28, 2025

(54) HIGH FREQUENCY NOISE FILTERING EARPLUG USING METASURFACE

(71) Applicant: KOREA UNIVERSITY RESEARCH AND BUSINESS FOUNDATION, Seoul (KR)

(72) Inventors: Young June Moon, Seoul (KR); Hyung Keun Chung, Seongnam-si (KR)

(73) Assignee: Korea University Research and Business Foundation, Seoul (KR)

( * ) Notice: Subject to any disclaimer, the term of this patent is extended or adjusted under 35 U.S.C. 154(b) by 266 days.

(21) Appl. No.: 17/773,212

(22) PCT Filed: Jun. 4, 2021

(86) PCT No.: PCT/KR2021/007041
§ 371 (c)(1),
(2) Date: Apr. 29, 2022

(87) PCT Pub. No.: WO2022/181888
PCT Pub. Date: Sep. 1, 2022

(65) Prior Publication Data
US 2023/0157895 A1    May 25, 2023

(30) Foreign Application Priority Data
Feb. 26, 2021  (KR) .................. 10-2021-0026497

(51) Int. Cl.
*A61F 11/08*  (2006.01)
*G10K 11/175*  (2006.01)
*H04R 1/10*  (2006.01)

(52) U.S. Cl.
CPC ............ *A61F 11/08* (2013.01); *G10K 11/175* (2013.01); *G10K 2210/3214* (2013.01)

(58) Field of Classification Search
CPC .......... A61F 11/08; A61F 11/00; A61F 11/06; A61F 11/085; G10K 11/175; G10K 11/16;
(Continued)

(56) References Cited

U.S. PATENT DOCUMENTS 3,157,750 A  *  11/1964  Weingartner .......... H04R 1/225
                                                              381/373
3,602,330 A  *  8/1971   Johnson ............... H04R 25/652
                                                              181/135
(Continued)

FOREIGN PATENT DOCUMENTS

CH          254 103 A       4/1948
CN        207166698 U       3/2018
(Continued)

OTHER PUBLICATIONS

Extended European search report issued on Sep. 15, 2023, in counterpart European Patent Application No. 21878759.6 (7 pages).
(Continued)

*Primary Examiner* — Edgardo San Martin
(74) *Attorney, Agent, or Firm* — NSIP Law

(57) ABSTRACT

Proposed is an earplug that can effectively reduce high-frequency noise using a metasurface. The high-frequency noise filtering earplug using a metasurface according to an embodiment of the present disclosure may include an eartip with an internal passage, an interference attenuation module having a damping passage for reducing noise and a first reflective cavity that is connected to the damping passage and reflects incident sound waves and transmits the sound waves to the damping passage, and a connecting tube installed between the eartip and the interference attenuation module to connect the internal passage and the damping passage to each other.

11 Claims, 7 Drawing Sheets

(58) Field of Classification Search
CPC ............... G10K 11/172; G10K 11/04; G10K 2210/3214
See application file for complete search history.

(56) References Cited

U.S. PATENT DOCUMENTS

| | | | | |
|---|---|---|---|---|
| 3,688,863 | A * | 9/1972 | Johnson | H04R 25/48 |
| | | | | 181/135 |
| 3,730,181 | A * | 5/1973 | Fling | A61F 11/08 |
| | | | | 128/868 |
| 4,407,389 | A * | 10/1983 | Johnson | H04R 25/652 |
| | | | | 381/328 |
| 4,441,576 | A * | 4/1984 | Allen | A61F 11/14 |
| | | | | 381/372 |
| 4,807,612 | A * | 2/1989 | Carlson | A61F 11/08 |
| | | | | 128/868 |
| 5,012,890 | A * | 5/1991 | Nagi | H04R 1/2826 |
| | | | | 381/353 |
| 5,832,094 | A | 11/1998 | Le Her | |
| 6,691,822 | B2 * | 2/2004 | Meussen | A61F 11/08 |
| | | | | 181/129 |
| 7,740,104 | B1 * | 6/2010 | Parkins | A61F 11/08 |
| | | | | 181/129 |
| 7,817,814 | B2 * | 10/2010 | Yang | H04R 1/1075 |
| | | | | 381/382 |
| 8,184,821 | B2 * | 5/2012 | Sung | H04R 1/1083 |
| | | | | 381/382 |
| 9,087,506 | B1 | 7/2015 | Kraft et al. | |
| 10,271,994 | B2 * | 4/2019 | Atherton | A61F 11/08 |
| 10,821,027 | B2 * | 11/2020 | Cobabe | H04R 1/1016 |
| 11,640,816 | B1 * | 5/2023 | Mathur | G10K 11/04 |
| | | | | 181/198 |
| 2006/0042867 | A1 | 3/2006 | Haussmann et al. | |
| 2009/0190771 | A1 | 7/2009 | Sung | |
| 2022/0079813 | A1 * | 3/2022 | Lawrence | G10K 11/162 |

FOREIGN PATENT DOCUMENTS

| | | |
|---|---|---|
| EP | 0 440 572 A1 | 8/1991 |
| KR | 10-1985-0005770 A | 9/1985 |
| KR | 10-1985-0001816 B1 | 12/1985 |
| WO | WO 2018/235254 A1 | 12/2018 |
| WO | WO 2020/028838 A1 | 2/2020 |

OTHER PUBLICATIONS

Korean Office Action issued on Jun. 7, 2023, in counterpart Korean Patent Application No. 10-2021-0026497 (6 pages in Korean).

* cited by examiner

[FIG. 1]
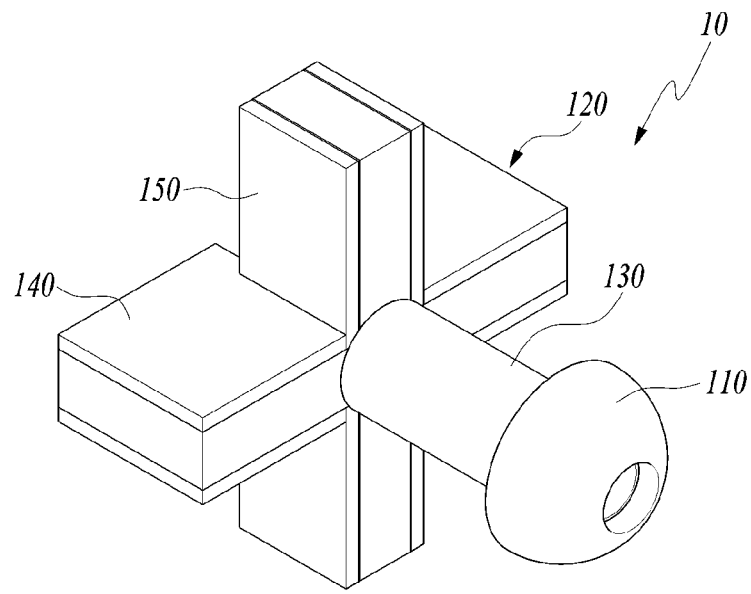
[FIG. 2]
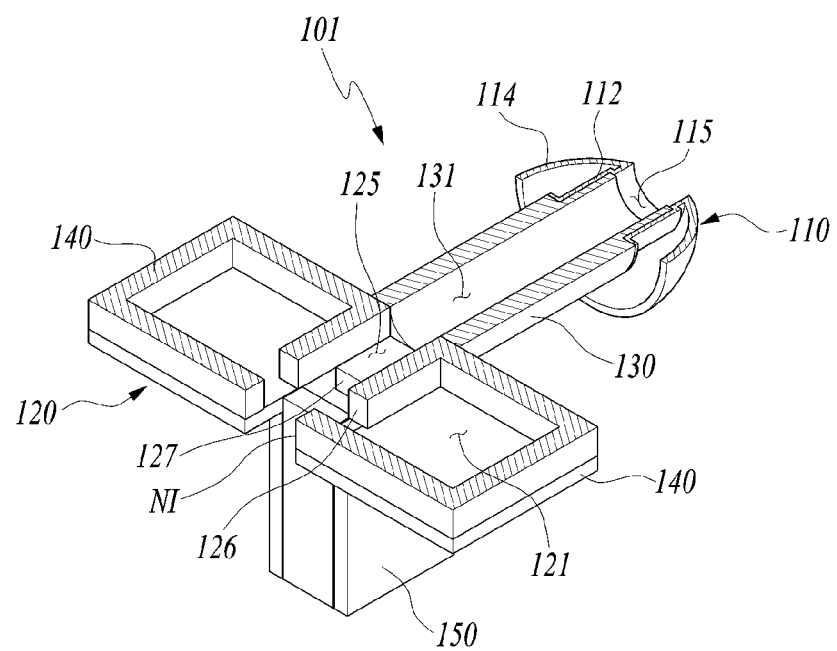

[FIG. 3]
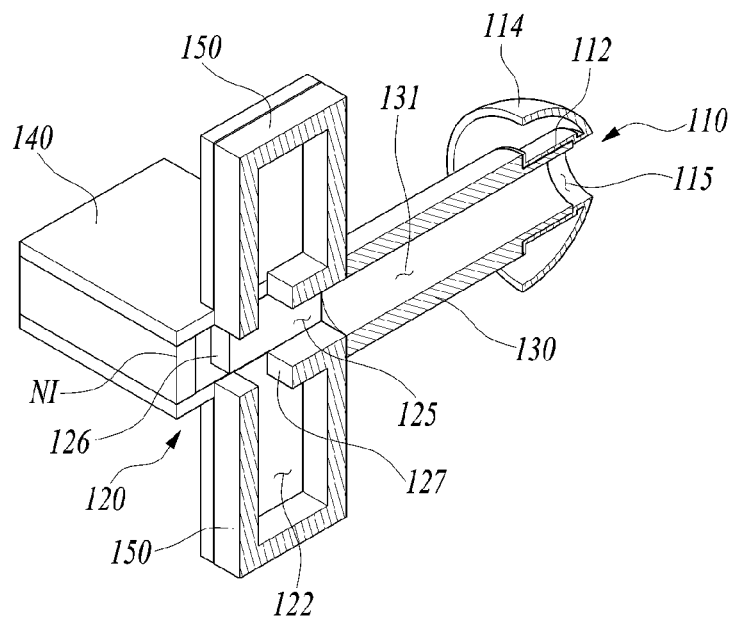
[FIG. 4]
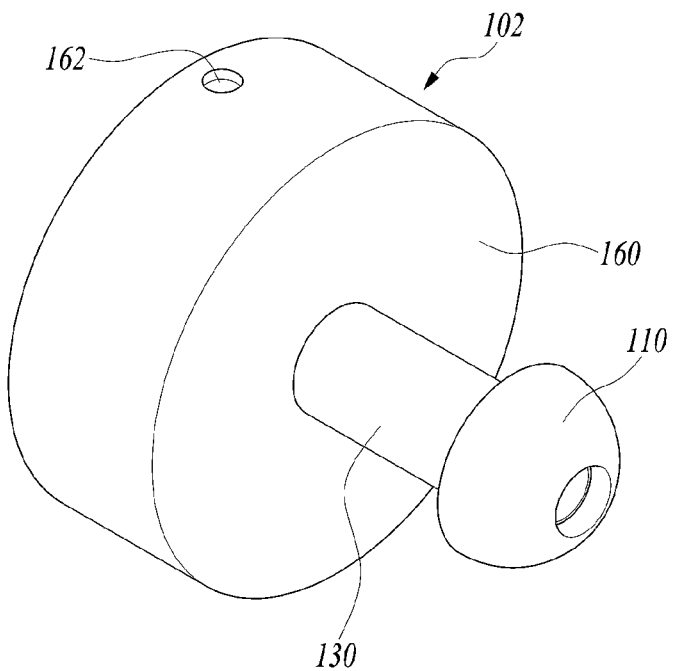

[FIG. 5]
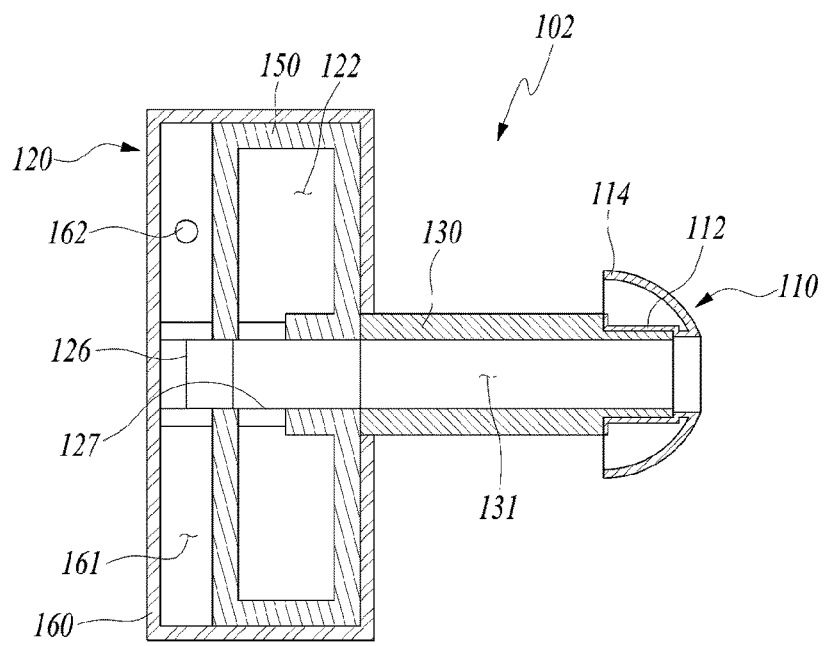
[FIG. 6]
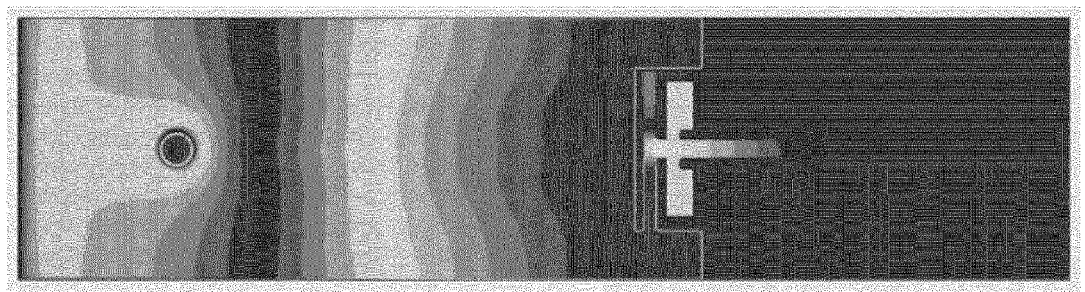
[FIG. 7]
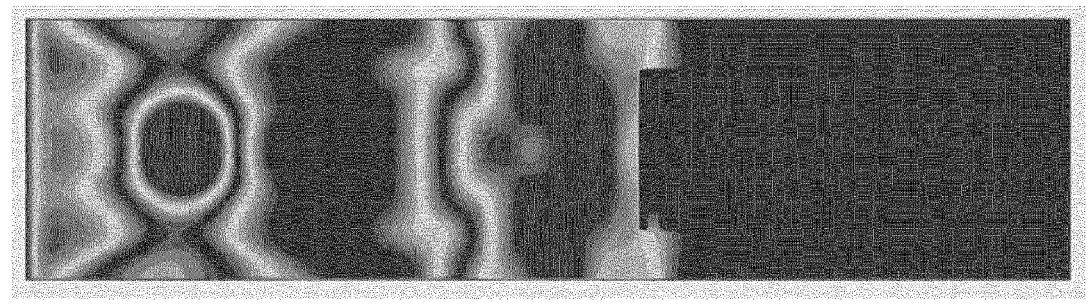

[FIG. 8]
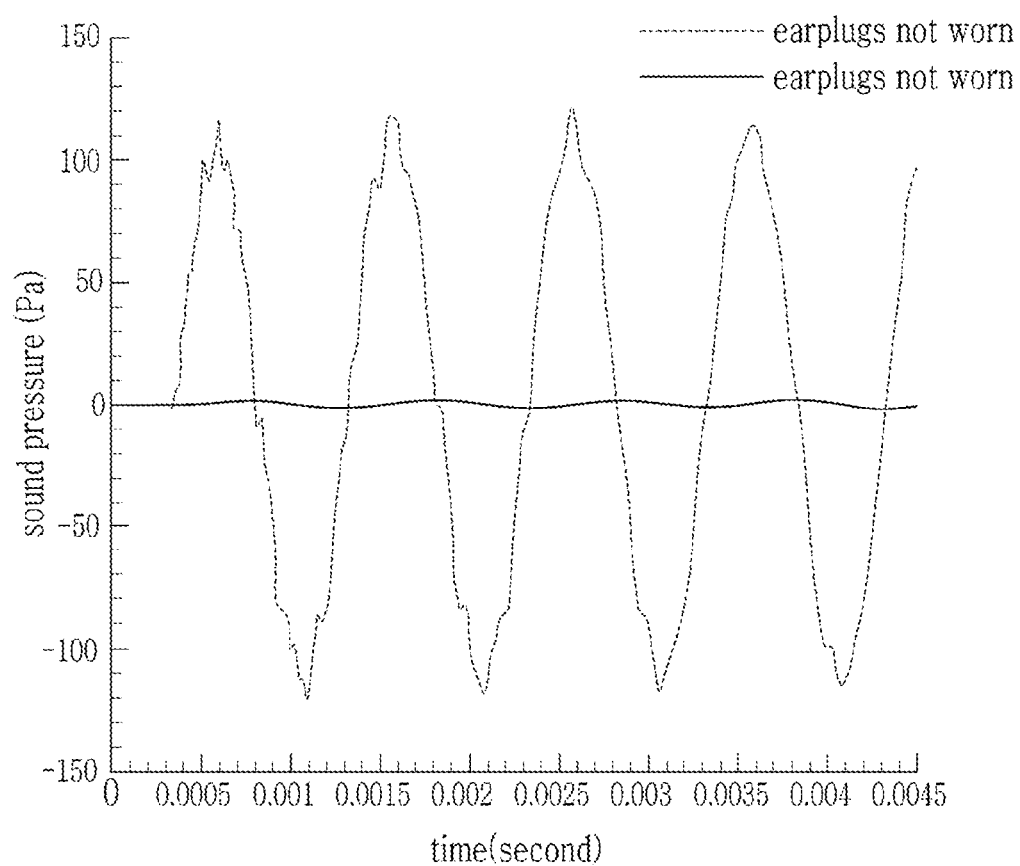

[FIG. 9]
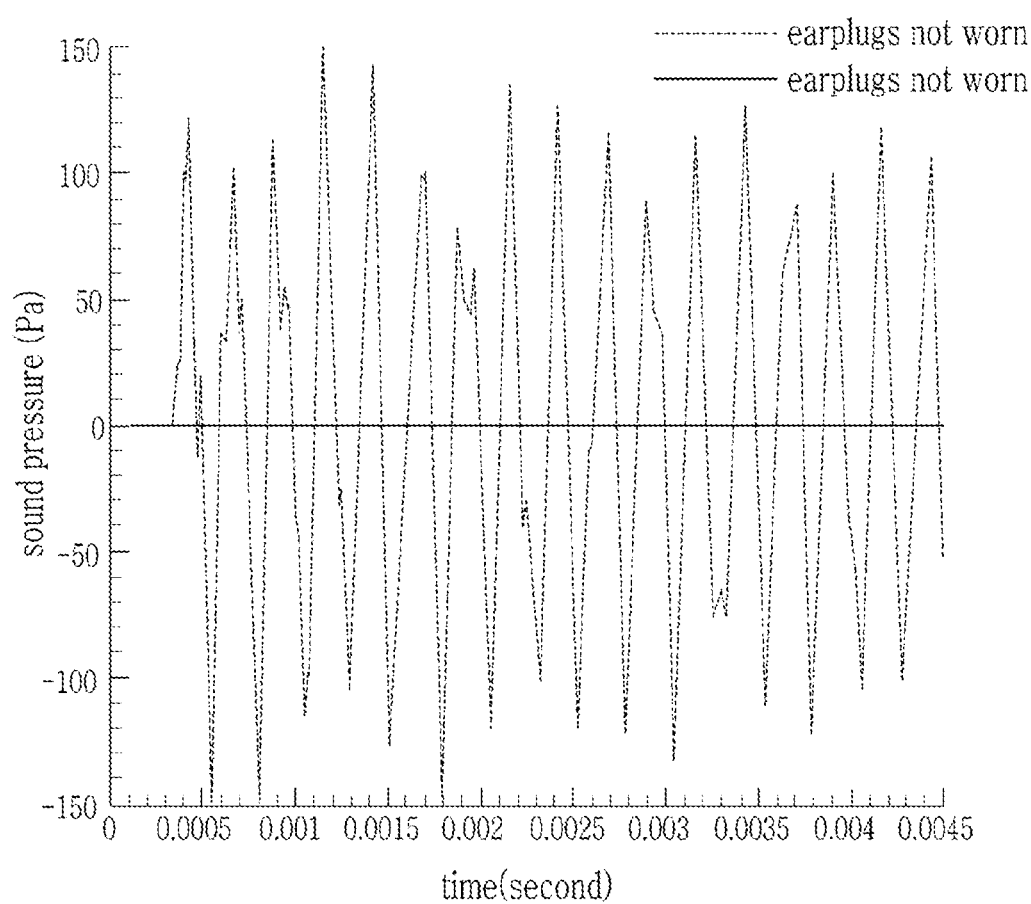

【FIG. 10】
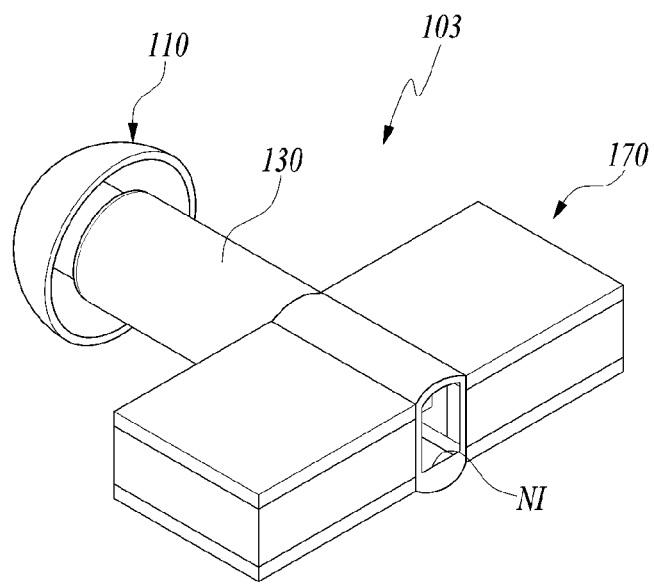
【FIG. 11】
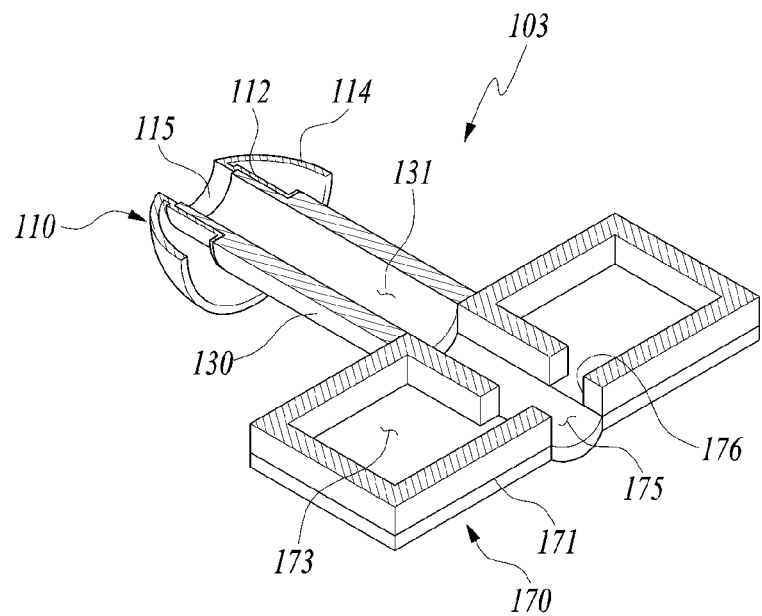

[FIG. 12]
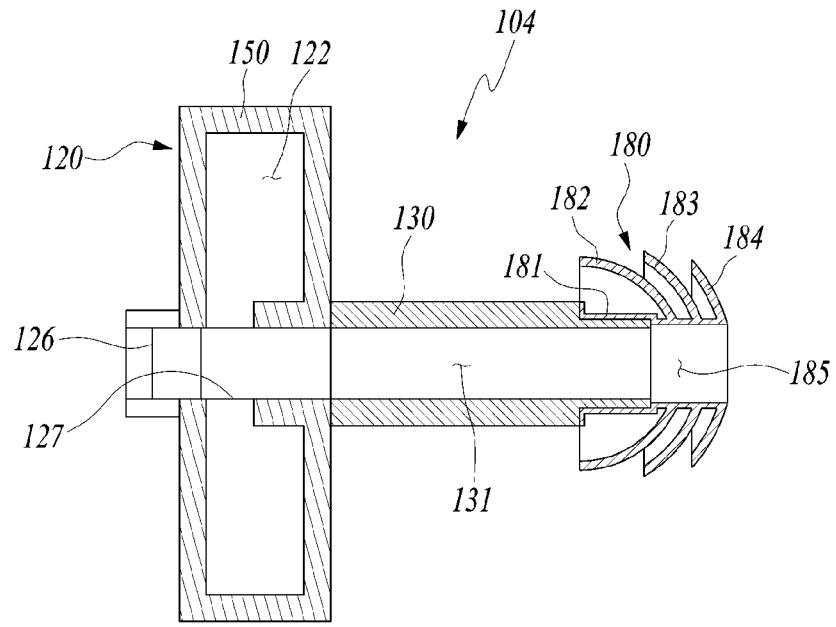
[FIG. 13]
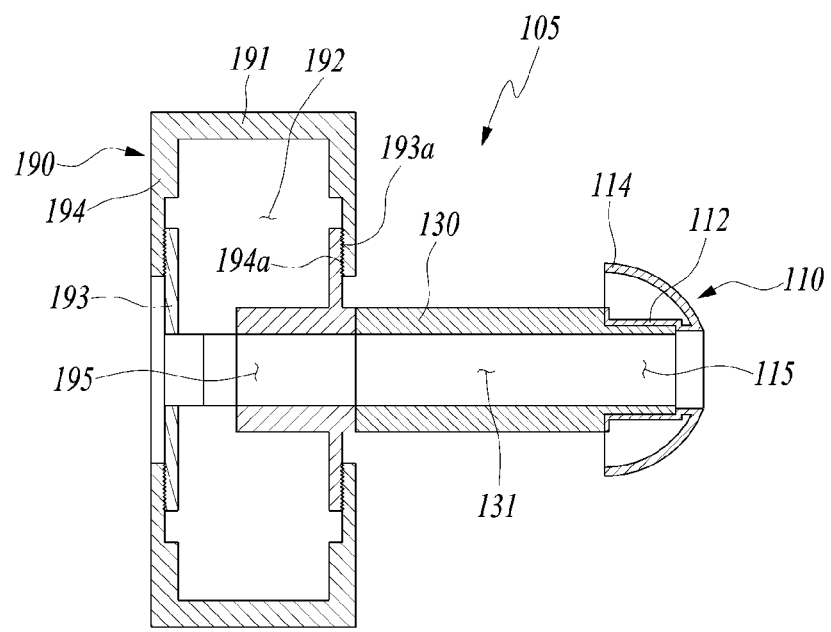

HIGH FREQUENCY NOISE FILTERING EARPLUG USING METASURFACE

CROSS REFERENCE TO RELATED APPLICATIONS

This application is a U.S. National Stage Application of International Application No. PCT/KR2021/007041, filed on Jun. 4, 2021, which claims the benefit under 35 USC 119(a) and 365(b) of Korean Patent Application No. 10-2021-0026497, filed on Feb. 26, 2021 in the Korean Intellectual Property Office, the entire disclosure of which is incorporated herein by reference for all purposes.

TECHNICAL FIELD

The present disclosure relates to an earplug and, more particularly, to an earplug that can reduce high-frequency noise using a metasurface.

BACKGROUND ART

In general, earplugs are worn on ears to protect a user's hearing from noise, to be used for blocking water from entering ears, and to improve concentration while working or studying. Recently, earplugs that block noise in a specific range through noise canceling technology have been released.

However, earplugs with a noise canceling function are expensive and require charging, which can be inconvenient. For earplugs at a relatively low price, the disadvantage is that their functions are very limited since they have limited functionality and are intended only for wearing comfort, sound insulation, and soundproofing. Also, there is a problem of communication difficulties because all bands of sound are blocked.

In the case of optional noise-shielding earplugs with a conventional external noise path, simply a sound absorbing material is used or a vortex is created during the movement of a sound wave by designing the path of the sound wave in a complicated way to reduce the noise. This structure has a problem in that the overall noise reduction amount is not large and it is difficult to shield the low-frequency sounds from the high-frequency sounds.

DISCLOSURE

Technical Problem

The present disclosure has been made keeping in mind the problems occurring in the related art, and an objective of the present disclosure is to provide an earplug that can effectively reduce high-frequency noise.

Technical Solution

A high-frequency noise filtering earplug using a metasurface according to an embodiment of the present disclosure may include: an eartip with an internal passage; an interference attenuation module having a damping passage for reducing noise and a first reflective cavity that is connected to the damping passage and reflects incident sound waves and transmits the sound waves to the damping passage; and a connecting tube installed between the eartip and the interference attenuation module to connect the internal passage and the damping passage.

The interference attenuation module according to an embodiment of the present disclosure may include a first damping protrusion protruding in the lateral direction of the damping passage, and a first reflective cavity may be formed inside the first damping protrusion.

The interference attenuation module according to an embodiment of the present disclosure may include two first damping protrusions, and the first damping protrusions may be spaced apart from each other with the damping passage interposed therebetween.

The interference attenuation module according to an embodiment of the present disclosure may include a second damping protrusion protruding in a direction crossing the first damping protrusion, and a second reflective cavity may be formed inside the second damping protrusion.

The second reflective cavity according to an embodiment of the present disclosure may have a smaller volume than the first reflective cavity.

A first opening connecting the first reflective cavity and the damping passage may be formed in the first reflective cavity according to an embodiment of the present disclosure, a second opening connecting the second reflective cavity and the damping passage may be formed in the second reflective cavity, and the first opening and the second opening may be spaced apart from each other in the longitudinal direction of the damping passage.

The first damping protrusion according to an embodiment of the present disclosure may be more protruding to the rear than the second damping protrusion.

The interference attenuation module according to an embodiment of the present disclosure may further include a casing surrounding the first damping protrusion and the second damping protrusion, and a noise inlet through which sound waves are introduced may be formed in the casing.

A third reflective cavity for reflecting sound waves may be formed between the casing and the first damping protrusion and the second damping protrusion according to an embodiment of the present disclosure.

The first damping protrusion according to an embodiment of the present disclosure may include a first body and a second body slidable to the first body, so that a volume of the first reflective cavity may be increased or decreased.

Advantageous Effects

As described above, the high-frequency noise filtering earplug using a metasurface according to an embodiment of the present disclosure has reflective cavities, which are metasurfaces on which high-frequency noise may be reflected, so that the incident high-frequency noise is reflected inside the reflective cavities, and the phase-shifted noise interferes with the noise incident in the damping passage, thus the high-frequency noise can be attenuated by interference.

DESCRIPTION OF DRAWINGS

FIG. 1 is a perspective view showing an earplug according to a first embodiment of the present disclosure;

FIG. 2 is a cutaway perspective view of the earplug according to the first embodiment of the present disclosure, cut in the transverse direction;

FIG. 3 is a cutaway perspective view of the earplug according to the first embodiment of the present disclosure, cut in the longitudinal direction;

FIG. 4 is a perspective view showing an earplug according to a second embodiment of the present disclosure;

FIG. 5 is a cross-sectional view of the earplug according to the second embodiment of the present disclosure;

FIG. 6 is a photograph showing the simulation results of emitting a 1000 Hz sound wave to the earplug according to the second embodiment of the present disclosure;

FIG. 7 is a photograph showing the simulation results of emitting a 4000 Hz sound wave to the earplug according to the second embodiment of the present disclosure;

FIG. 8 is a graph showing the results of emitting the 1000 Hz sound wave in a state in which earplug according to the second embodiment of the present disclosure is worn and in a state in which it is not worn;

FIG. 9 is a graph showing the results of emitting the 4000 Hz sound wave in a state in which earplug according to the second embodiment of the present disclosure is worn and in a state in which it is not worn;

FIG. 10 is a perspective view showing an earplug according to a third embodiment of the present disclosure;

FIG. 11 is a cutaway perspective view of the earplug according to the third embodiment of the present disclosure;

FIG. 12 is a cross-sectional view showing an earplug according to a fourth embodiment of the present disclosure; and FIG. 13 is a cross-sectional view showing an earplug according to a fifth embodiment of the present disclosure.

MODE FOR INVENTION

While the present disclosure may be modified in various ways and take on various alternative forms, specific embodiments thereof are shown and described in detail below. However, it should be understood that there is no intent to limit the present disclosure to the particular forms disclosed, but on the contrary, the present disclosure covers all modifications, equivalents, and alternatives falling within the spirit and scope of the present disclosure.

The terminology used herein to describe embodiments of the present disclosure is not intended to limit the scope of the present disclosure. The singular expression includes the plural expression unless the context clearly dictates otherwise. It should be further understood that the terms "comprise", "include", and/or "have", when used herein, specify the presence of stated features, numbers, steps, operations, elements, components, and/or groups thereof but do not preclude the presence or addition of one or more other features, numbers, steps, operations, elements, components, and/or groups thereof.

Hereinafter, preferred embodiments of the present disclosure will be described in detail with reference to the accompanying drawings. In this case, it should be noted that in the accompanying drawings, the same components are denoted by the same reference numerals as much as possible. In addition, detailed descriptions of well-known functions and configurations that may obscure the gist of the present disclosure will be omitted. For the same reason, some components are exaggerated, omitted, or schematically illustrated in the accompanying drawings.

Hereinafter, a gripper having a fastening function according to a first embodiment of the present disclosure will be described.

FIG. 1 is a perspective view showing an earplug according to the first embodiment of the present disclosure, FIG. 2 is a cutaway perspective view of the earplug according to the first embodiment of the present disclosure, cut in the transverse direction, and FIG. 3 is a cutaway perspective view of the earplug according to the first embodiment of the present disclosure, cut in the longitudinal direction.

When described with reference to FIGS. 1 to 3, an earplug 101 according to the first embodiment includes an eartip 110, an interference attenuation module 120, and a connecting tube 130. The earplug 101 according to the present embodiment may be made of an earplug that blocks high-frequency noise. In this description, high-frequency noise means noise between 1000 Hz and 8000 Hz. High-frequency noise is high-frequency noise generated in construction sites, factories, and dental clinics, and may cause hearing loss if exposed for a long time. Also, in this description, a metasurface is defined as an artificial surface or shape added for reflection of sound waves.

The eartip 110 may have a structure similar to the eartip of a general canal type earphone. The eartip 110 may be inserted inside a user's ear, in particular, the ear canal. The eartip 110 includes a tip tube 112 coupled to the connecting tube 130 and a sleeve 114 that protrudes outward from the tip tube 112 and is in close contact with the ear canal. The eartip 110 is formed to be detachable to the connecting tube 130.

Meanwhile, the tip tube 112 is made of a cylindrical tube and an internal passage 115 connected to the connecting tube 130 is formed on the inside of the tip tube 112. A low-frequency sound wave such as an unattenuated voice may be transmitted through the internal passage 115. The sleeve 114 has an arc-shaped curved plate structure and protrudes backward from the tip tube 112. The sleeve 114 is in close contact with the user's ear canal to prevent noise from penetrating into the ear canal.

The connecting tube 130 is made of a cylindrical tube and connects the eartip 110 and the interference attenuation module 120. An intermediate passage 131 is formed inside the connecting tube 130, and the sound wave transmitted from the interference attenuation module 120 may be transmitted to the eartip 110 through the connecting tube 130.

The interference attenuation module 120 transmits sound to the connecting tube 130 and may include a damping passage 125 for reducing noise, a first damping protrusion 140 protruding in the lateral direction of the damping passage 125, and a second damping protrusion 150 protruding in the direction crossing the first damping protrusion 140.

The two first damping protrusions 140 protrude in opposite directions and are spaced apart from each other with the damping passage 125 interposed therebetween. The second damping protrusion 150 is protruded to vertically intersect with the first damping protrusion 140, and the two second damping protrusions 150 are spaced apart from each other with the damping passage 125 interposed therebetween. The first damping protrusions 140 are arranged in a line parallel to each other, and the second damping protrusions 150 are also arranged in a line parallel to each other. Accordingly, the first damping protrusions 140 and the second damping protrusions 150 may be combined and arranged in a cross shape.

In addition, the first damping protrusion 140 has the same length as the second damping protrusion 150, and the first damping protrusion 140 may protrude further rearward than the second damping protrusion 150. In the present description, the front refers to a direction toward the front end of the eartip 110, and the rear refers to a direction in which the interference attenuation module is located.

Inside the first damping protrusion 140, a first reflective cavity 121 that is connected to the damping passage 125 and reflects the incident sound waves and transmits the sound waves to the damping passage 125 is formed. Also, inside the second damping protrusion 140, a second reflective cavity 122 that is connected to the damping passage 125 and reflects the incident sound waves and transmits the sound waves to the damping passage 125 is formed. The two first reflective cavities 121 and the two second reflective cavities 122 may be connected in a cross shape via the damping passage 125 as a medium. The first reflective cavity 121 and the second reflective cavity 122 are artificial metasurfaces added for reflection of sound waves, and the high-frequency noise introduced into the first reflective cavity 121 and the second reflective cavity 122 is phase-shifted.

The damping passage 125 is positioned between the first damping protrusion 140 and the second damping protrusion 150, and has a noise inlet (NI) that is opened to the rear and into which noise is incident. Accordingly, the earplug according to the present embodiment is of an open type through which noise may be introduced.

A first opening 126 connecting the first reflective cavity 121 and the damping passage 125 is formed in the first reflective cavity 121, and a second opening 127 connecting the second reflective cavity 122 and the damping passage 125 is formed in the second reflective cavity 122. The first opening 126 and the second opening 127 are spaced apart from each other in the longitudinal direction of the damping passage 125, and the second opening 127 is located more forward than the first opening 126.

Meanwhile, the second reflective cavity 122 has a smaller volume than the first reflective cavity 121, and accordingly, the first reflective cavity 121 and the second reflective cavity 122 may reflect sound waves of different frequencies. The first reflective cavity 121 and the second reflective cavity 122 that are metasurfaces may be formed to reflect sound waves of a specific frequency.

Some of the noise introduced through the damping passage 125 is introduced into the first reflective cavity 121 through the first opening 126, and high-frequency waves among the introduced sound waves are reflected from the first reflective cavity 121 and phase-shifted to be discharged to the damping passage 125 through the first opening 126.

In addition, some of the noise introduced through the damping passage 125 is introduced into the second reflective cavity 122 through the second opening 127, and high-frequency waves among the introduced sound waves are reflected from the second reflective cavity 122 and phase-shifted to be discharged to the damping passage 125 through the second opening 127.

Sound waves reflected from the first reflective cavity 121 and the second reflective cavity 122 may interfere with high-frequency sound waves incident from the damping passage, so that destructive interference of the noise may occur. The frequency of the attenuated sound wave may be adjusted by changing the structures of the first reflective cavity 121 and the second reflective cavity 122.

In general, noise generated in construction sites, factories, and dental clinics is high-frequency sound waves, and these high-frequency noises cause hearing loss. However, communication is necessary during work, so if you wear earplugs that block all sounds, communication during work is impossible, which reduces work efficiency. The earplug according to the present embodiment attenuates only high-frequency noise among noises introduced into the damping passage and passes the voice through, so that it is possible to communicate easily while preventing hearing loss.

Hereinafter, an earplug according to a second embodiment of the present disclosure will be described.

FIG. 4 is a perspective view showing the earplug according to the second embodiment of the present disclosure, and FIG. 5 is a cross-sectional view of the earplug according to the second embodiment of the present disclosure.

Since the earplug 102 according to the second embodiment has the same structure as the earplug 102 according to the first embodiment except for a casing 160, a redundant description of the same configuration will be omitted.

An interference attenuation module 120 transmits sound to a connecting tube 130 and may include a damping passage 125 for reducing noise, a first damping protrusion 140 protruding in the lateral direction of the damping passage 125, a second damping protrusion 150 protruding in the direction crossing the first damping protrusion 140, and the casing 160 surrounding the first damping protrusion 140 and the second damping protrusion 150.

Inside the first damping protrusion 140, a first reflective cavity 121 that is connected to the damping passage 125 and reflects the incident sound waves and transmits the sound waves to the damping passage 125 is formed. Also, inside the second damping protrusion 140, a second reflective cavity 122 that is connected to the damping passage 125 and reflects the incident sound waves and transmits the sound waves to the damping passage 125 is formed. The first reflective cavity 121 and the second reflective cavity 122 may be connected in a cross shape via the damping passage 125 as a medium.

The casing 160 has a cylindrical shape, and a noise inlet 162 through which sound waves are introduced is formed in the casing 160. The noise inlet 162 is formed on the outer peripheral surface of the casing 160 and is located at the rear of the second damping protrusion 150. Meanwhile, between the casing 160 and the first damping protrusion 140 and the second damping protrusion 150, a third reflective cavity 161 from which a sound wave is reflected is formed.

Accordingly, the sound waves introduced into the noise inlet 162 are reflected once from the third reflective cavity 161 and then flow into the first reflective cavity 121 and the second reflective cavity 122 through the damping passage 125. Noise may be reduced through destructive interference in the damping passage 125.

FIG. 6 is a photograph showing the simulation results of emitting a 1000 Hz sound wave to the earplug according to the second embodiment of the present disclosure, and FIG. 7 is a photograph showing the simulation results of emitting a 4000 Hz sound wave to the earplug according to the second embodiment of the present disclosure.

As shown in FIG. 6, the 1000 Hz sound wave does not pass through the earplug 102, and the 4000 Hz sound wave is blocked more stably by the earplug 102.

FIG. 8 is a graph showing the results of emitting the 1000 Hz sound wave in a state in which earplug according to the second embodiment of the present disclosure is worn and in a state in which it is not worn, and FIG. 9 is a graph showing the results of emitting the 4000 Hz sound wave in a state in which earplug according to the second embodiment of the present disclosure is worn and in a state in which it is not worn.

As shown in FIG. 8, when the earplug is worn, only a small change in pressure appears inside the earplug by passing only a very small volume of the 1000 Hz sound wave, and as shown in FIG. 9, 4000 Hz sound wave is mostly blocked by the earplug 102, so there is little change in pressure.

Hereinafter, an earplug according to a third embodiment of the present disclosure will be described.

FIG. 10 is a perspective view showing the earplug according to the third embodiment of the present disclosure, and FIG. 11 is a cutaway perspective view of the earplug according to the third embodiment of the present disclosure.

When described with reference to FIGS. 10 and 11, since the earplug 103 according to the third embodiment has the same structure as the earplug according to the first embodiment except for an interference attenuation module 170, a redundant description of the same configuration will be omitted.

The interference attenuation module 170 transmits sound to a connecting tube and may include a damping passage 175 for reducing noise, a first damping protrusion 171 protruding in the lateral direction of the damping passage 175. A first reflective cavity 173 is formed inside the first damping protrusion 171 that is connected to the damping passage 175 and reflects the incident sound waves and transmits the sound waves to the damping passage 175.

A first opening 176 connecting the first reflective cavity 173 and the damping passage 175 is formed in the first reflective cavity 173. The two first damping protrusions 171 protrude in opposite directions and are arranged in parallel with the damping passage 175 therebetween and are connected in a line. The damping passage 175 is positioned between the first damping protrusion 171 and the second damping protrusion, and has a noise inlet (NI) that is opened to the rear and into which noise is incident.

Accordingly, the sound wave introduced into the noise inlet NI is introduced into the first reflective cavity 173 and reflected, and noise may be reduced through destructive interference in the damping passage 175.

Hereinafter, an earplug according to a fourth embodiment of the present disclosure will be described.

FIG. 12 is a cross-sectional view showing the earplug according to the fourth embodiment of the present disclosure.

When described with reference to FIG. 12, since the earplug 104 according to the present embodiment has the the same structure as the earplug according to the first embodiment except for the eartip 180, a redundant description of the same configuration will be omitted.

The eartip 180 includes a tip tube 181 coupled to a connecting tube and a plurality of sleeves 182, 183, and 184 that protrude outward from the tip tube 181 and are in close contact with the ear canal. The eartip 180 is formed to be detachable to the connecting tube 130.

The tip tube 181 is made of a cylindrical tube and is fitted to the connecting tube 130. An internal passage 185 connected to the connecting tube 130 is formed on the inside of the tip tube 181, and low-frequency sound waves such as unattenuated voice may be transmitted through the internal passage 185.

The sleeves 182, 183, and 184 have an arc-shaped curved structure and protrude rearward from the tip tube 181. The plurality of sleeves 182, 183, and 184 may protrude from the tip tube 181. As such, when the eartip 180 includes the plurality of sleeves 182, 183, and 184, the sleeves 182, 183, and 184 are more closely attached to the ear canal, thereby preventing noise from penetrating into the ear canal.

Hereinafter, an earplug according to a fifth embodiment of the present disclosure will be described. FIG. 13 is a cross-sectional view showing the earplug according to the fifth embodiment of the present disclosure.

When described with reference to FIG. 13, since the earplug 105 according to the present fifth embodiment has the same structure as the earplug according to the first embodiment except for a damping protrusion, a redundant description of the same configuration will be omitted.

An interference attenuation module 190 transmits sound to a connecting tube 130 and may include a damping passage 195 for reducing noise, a first damping protrusion 191 protruding in the lateral direction of the damping passage 195, and a second damping protrusion protruding in the direction crossing the first damping protrusion 191.

Inside the first damping protrusion 191, a first reflective cavity 192 that is connected to the damping passage 195 and reflects the incident sound waves and transmits the sound waves to the damping passage is formed. Also, a second reflective cavity is formed inside the second damping protrusion. The first reflective cavity 192 and the second reflective cavity may be connected in a cross shape via the damping passage as a medium. Since the first damping protrusion 191 and the second damping protrusion have a similar structure, the description of the first damping protrusion 191 will replace the description of the second damping protrusion.

The first damping protrusion 191 includes a first body 193 and a second body 194 slidable to the first body 193, and thus the volume of the first reflective cavity 192 may be increased or decreased. A first concave-convex portion 193a is formed on the outer circumferential surface of the first body 193, and a second concave-convex portion 194a fitted to the first concave-convex portion 193a may be formed on the inner circumferential surface of the second body 194. Accordingly, the second body 194 slides in the first body 193 to change the volume of the first reflective cavity 192, and when the volume of the first reflective cavity 192 is changed, the frequency of the attenuated sound wave may be changed.

In the above, an embodiment of the present disclosure has been described, however, those of ordinary skill in the art will be able to variously modify and change the present disclosure by supplementing, changing, deleting, or adding components within the scope that does not depart from the spirit of the present disclosure described in the claims, and this will also be included within the scope of the present disclosure.

The invention claimed is:

1. A high-frequency noise filtering earplug using a metasurface, the earplug comprising:
    an eartip with an internal passage;
    an interference attenuation module having a damping passage for reducing noise and a first reflective cavity that is connected to the damping passage and reflects incident sound waves and transmits the sound waves to the damping passage; and
    a connecting tube installed between the eartip and the interference attenuation module to connect the internal passage and the damping passage to each other,
    wherein the interference attenuation module comprises a first damping protrusion protruding in a lateral direction of the damping passage and a second damping protrusion protruding to intersect perpendicularly with the first damping protrusion.

2. The high-frequency noise filtering earplug using a metasurface of claim 1, wherein the first reflective cavity is formed inside the first damping protrusion.

3. The high-frequency noise filtering earplug using a metasurface of claim 1, wherein the interference attenuation module includes two first damping protrusions spaced apart from each other with the damping passage interposed therebetween.

4. The high-frequency noise filtering earplug using a metasurface of claim 1, wherein a second reflective cavity is formed inside the second damping protrusion.

5. The high-frequency noise filtering earplug using a metasurface of claim 4, wherein the second reflective cavity has a smaller volume than the first reflective cavity.

6. The high-frequency noise filtering earplug using a metasurface of claim 5, wherein a first opening connecting the first reflective cavity and the damping passage to each other is formed in the first reflective cavity, a second opening connecting the second reflective cavity and the damping passage to each other is formed in the second reflective cavity, and the first opening and the second opening are spaced apart from each other in a longitudinal direction of the damping passage.

7. The high-frequency noise filtering earplug using a metasurface of claim 1, wherein the first damping protrusion is more protruding to a rear than the second damping protrusion.

8. The high-frequency noise filtering earplug using a metasurface of claim 1, wherein the interference attenuation module further includes a casing surrounding the first damping protrusion and the second damping protrusion, and a noise inlet through which sound waves are introduced is formed in the casing.

9. The high-frequency noise filtering earplug using a metasurface of claim 4, wherein a third reflective cavity for reflecting sound waves is formed between the casing and the first damping protrusion and the second damping protrusion.

10. The high-frequency noise filtering earplug using a metasurface of claim 1, wherein the first damping protrusion includes a first body and a second body slidable to the first body, and a volume of the first reflective cavity is configured to be increased or decreased.

11. A high-frequency noise filtering earplug using a metasurface, the earplug comprising:
  an eartip with an internal passage;
  an interference attenuation module comprising a damping passage for reducing noise and a first reflective cavity that is connected to the damping passage and reflects incident sound waves and transmits the sound waves to the damping passage; and
  a connecting tube installed between the eartip and the interference attenuation module to connect the internal passage and the damping passage to each other,
wherein the interference attenuation module comprises:
  a first damping protrusion protruding in a lateral direction of the damping passage and the first reflective cavity formed inside the first damping protrusion;
  a second damping protrusion protruding in a direction crossing the first damping protrusion and a second reflective cavity formed inside the second damping protrusion;
  a casing surrounding the first and second damping protrusions; and
  a noise inlet formed in the casing and configured to allow sound waves to enter.

* * * * *